United States Patent
Luttrull et al.

(10) Patent No.: US 9,381,115 B2
(45) Date of Patent: Jul. 5, 2016

(54) SYSTEM AND PROCESS FOR RETINA PHOTOTHERAPY

(75) Inventors: Jeffrey K. Luttrull, Ojai, CA (US); Benjamin Margolis, Pomona, CA (US)

(73) Assignee: Ojai Retinal Technology, LLC, Ojai, CA (US)

(*) Notice: Subject to any disclaimer, the term of this patent is extended or adjusted under 35 U.S.C. 154(b) by 438 days.

(21) Appl. No.: 13/481,124

(22) Filed: May 25, 2012

(65) Prior Publication Data

US 2013/0317570 A1 Nov. 28, 2013

(51) Int. Cl.
*A61N 5/06* (2006.01)
*A61F 9/008* (2006.01)

(52) U.S. Cl.
CPC ... *A61F 9/00821* (2013.01); *A61F 2009/00844* (2013.01); *A61F 2009/00863* (2013.01)

(58) Field of Classification Search
CPC .................................. A61B 17/00; A61N 5/06
USPC ............................................ 606/4–6; 607/89
See application file for complete search history.

(56) References Cited

U.S. PATENT DOCUMENTS

| | | | |
|---|---|---|---|
| 3,408,593 A | 10/1968 | Hurwitz, Jr. |
| 4,048,011 A | 9/1977 | Kovin et al. |
| 4,176,325 A | 11/1979 | Kajimura et al. |
| 4,194,114 A | 3/1980 | Pankratov et al. |
| 4,410,365 A | 10/1983 | Glukhovsky et al. |
| 4,695,733 A | 9/1987 | Pesavento |
| 4,730,335 A | 3/1988 | Clark et al. |
| 4,791,634 A | 12/1988 | Miyake |
| 4,865,029 A | 9/1989 | Pankratov et al. |
| 4,879,722 A | 11/1989 | Dixon et al. |
| 4,930,504 A | 6/1990 | Diamantopoulos et al. |
| 4,933,944 A | 6/1990 | McGraw |
| 4,935,931 A | 6/1990 | McGraw |
| 4,961,079 A | 10/1990 | Owens et al. |
| 4,967,416 A | 10/1990 | Esterowitz et al. |
| 5,037,421 A | 8/1991 | Boutacoff et al. |
| 5,067,951 A | 11/1991 | Greve |
| 5,085,492 A | 2/1992 | Kelsoe et al. |
| 5,088,803 A | 2/1992 | Buzawa |
| 5,147,354 A | 9/1992 | Boutacoff et al. |

(Continued)

FOREIGN PATENT DOCUMENTS

| | | | |
|---|---|---|---|
| WO | WO 2006005038 A2 | 1/2006 |
| WO | WO 2007035855 A2 | 3/2007 |
| WO | WO 2007106521 A2 | 9/2007 |

OTHER PUBLICATIONS

Luttrull et al. Subthreshold diode micropulse panretinal photocoagulation for proliferative diabetic retinopathy. Eye (2007), 1-6 © 2007 Nature Publishing Group, www.nature.com/eye.*

(Continued)

*Primary Examiner* — William Thomson
*Assistant Examiner* — Victor Shapiro
(74) *Attorney, Agent, or Firm* — Kelly & Kelley, LLP

(57) ABSTRACT

A system and process for treating retinal diseases includes passing a laser light beam through an optical lens or mask to optically shape the light beam. The light beam is applied to at least a portion of the retina. Due to the selected parameters of the laser light beam pulse length, power and duty cycle, the laser light beam can be applied to substantially the entire retina, including the fovea, without damaging retinal or foveal tissue, while still attaining the benefits of retinal photocoagulation.

31 Claims, 7 Drawing Sheets

(56) References Cited

U.S. PATENT DOCUMENTS

| | | | |
|---|---|---|---|
| 5,372,595 | A | 12/1994 | Gaasterland et al. |
| 5,394,199 | A | 2/1995 | Flower |
| 5,430,756 | A | 7/1995 | Hanihara |
| 5,520,680 | A | 5/1996 | Shapshay et al. |
| 5,651,019 | A | 7/1997 | Goldberg et al. |
| 5,982,789 | A | 11/1999 | Marshall et al. |
| 6,066,128 | A | 5/2000 | Bahmanyar et al. |
| 6,208,769 | B1 | 3/2001 | Pankratov |
| 6,222,869 | B1 | 4/2001 | Marshall et al. |
| 6,327,291 | B1 | 12/2001 | Marshall |
| 6,377,599 | B1 | 4/2002 | Marshall |
| 6,540,391 | B2 | 4/2003 | Lanzetta et al. |
| 6,681,185 | B1 | 1/2004 | Young et al. |
| 6,715,877 | B2 | 4/2004 | Molebny |
| 6,733,490 | B1 | 5/2004 | Falsini et al. |
| 6,813,942 | B1 | 11/2004 | Vozhdaev et al. |
| 6,889,695 | B2 | 5/2005 | Pankratov et al. |
| 6,942,655 | B2 * | 9/2005 | Peyman ............... 606/4 |
| 7,227,196 | B2 | 6/2007 | Burgener, II et al. |
| 7,229,435 | B2 * | 6/2007 | Nakamura ............ 606/4 |
| 7,387,785 | B1 | 6/2008 | Rudin et al. |
| 7,452,081 | B2 | 11/2008 | Wiltberger et al. |
| 7,645,276 | B2 | 1/2010 | Pankratov et al. |
| 7,763,828 | B2 | 7/2010 | Talwar et al. |
| 7,766,903 | B2 | 8/2010 | Blumenkranz et al. |
| 7,766,904 | B2 | 8/2010 | Mc Gowan, Sr. et al. |
| 7,771,417 | B2 | 8/2010 | Telfair et al. |
| 7,909,816 | B2 | 3/2011 | Buzawa |
| 8,454,161 | B2 | 6/2013 | Su et al. |
| 2002/0099363 | A1 | 7/2002 | Woodward et al. |
| 2002/0120255 | A1 | 8/2002 | Sotiropoulos et al. |
| 2002/0165525 | A1 | 11/2002 | Nakamura |
| 2004/0098070 | A1 * | 5/2004 | Mohr et al. ............ 607/89 |
| 2007/0173793 | A1 * | 7/2007 | Rathjen ............... 606/4 |
| 2007/0213693 | A1 * | 9/2007 | Plunkett .............. 606/6 |
| 2008/0015553 | A1 | 1/2008 | Zacharias |
| 2010/0152716 | A1 | 6/2010 | Previn et al. |
| 2010/0168724 | A1 | 7/2010 | Sramek et al. |
| 2010/0249760 | A1 | 9/2010 | Blumenkranz et al. |
| 2010/0290007 | A1 | 11/2010 | Van de Velde |
| 2011/0196350 | A1 | 8/2011 | Friedman et al. |
| 2013/0116672 | A1 | 5/2013 | Yee |

OTHER PUBLICATIONS

Yeow, J.T.W. et al.; Micromachined 2-D scanner for 3-D optical coherence tomography; Sensors and Actuators A: Physical, vol. 117, Issue 2, Jan. 14, 2005, pp. 331-340; Elsevier.

Luttrull, JK et al.; Subthreshold diode micropulse panretinal photocoagulation for proliferative diabetic retinopathy Eye (2007), 1-6; Eye advance online publication Jan. 16, 2009.

Luttrull, J K et al.; Subthreshold diode micropulse photocoagulation for the treatment of clinically significant diabetic macular oedema; Br J Ophthalmol 2005; 89:74-80.

Luttrull, Jeffrey K., MD et al.; Serial Optical Coherence Tomography of Subthreshold Diode Laser Micropulse Photocoagulation for Diabetic Macular Edema; Ophthalmic Surgery, Lasers & Imaging; Sep./Oct. 2006; vol. 37, No. 5; pp. 370-377.

Luttrull, J K et al.; Subthreshold diode micropulse photocoagulation for the treatment of clinically significant diabetic macular oedema; Eye (2009) Macmillan Publishers Limited 2009.

* cited by examiner

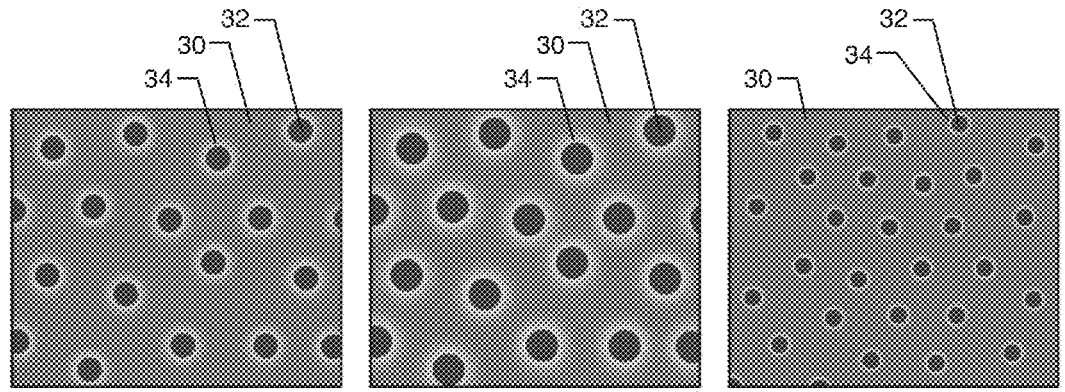
FIG. 2A PRIOR ART
FIG. 2B PRIOR ART
FIG. 2C PRIOR ART
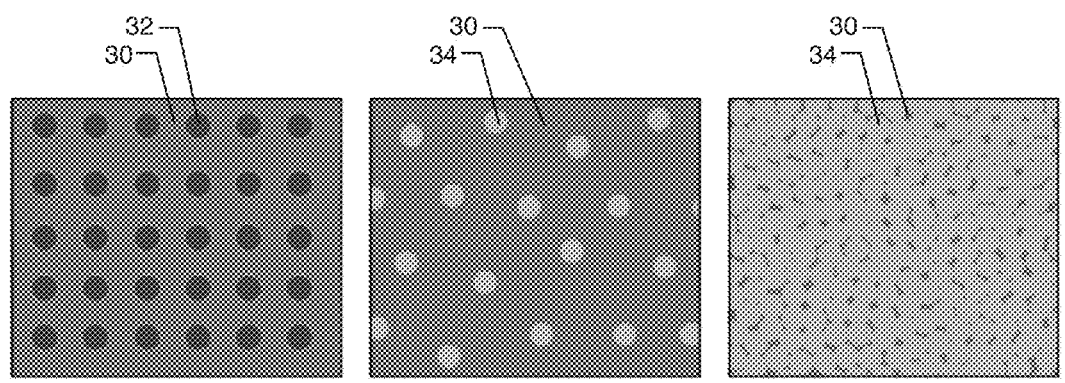
FIG. 2D PRIOR ART
FIG. 2E
FIG. 2F

SYSTEM AND PROCESS FOR RETINA PHOTOTHERAPY

BACKGROUND OF THE INVENTION

The present invention generally relates to phototherapy or photostimulation of biological tissue, such as laser retinal photocoagulation therapy. More particularly, the present invention is directed to a system and process for treating retinal diseases and disorders by using harmless, subthreshold phototherapy or photostimulation of the retina.

Complications of diabetic retinopathy remain a leading cause of vision loss in people under sixty years of age. Diabetic macular edema is the most common cause of legal blindness in this patient group. Diabetes mellitus, the cause of diabetic retinopathy, and thus diabetic macular edema, is increasing in incidence and prevalence worldwide, becoming epidemic not only in the developed world, but in the developing world as well. Diabetic retinopathy may begin to appear in persons with Type I (insulin-dependent) diabetes within three to five years of disease onset. The prevalence of diabetic retinopathy increases with duration of disease. By ten years, 14%-25% of patients will have diabetic macular edema. By twenty years, nearly 100% will have some degree of diabetic retinopathy. Untreated, patients with clinically significant diabetic macular edema have a 32% three-year risk of potentially disabling moderate visual loss.

Until the advent of thermal retinal photocoagulation, there was generally no effective treatment for diabetic retinopathy. Using photocoagulation to produce photothermal retinal burns as a therapeutic maneuver was prompted by the observation that the complications of diabetic retinopathy were often less severe in eyes with preexisting retinal scarring from other causes. The Early Treatment of Diabetic Retinopathy Study demonstrated the efficacy of argon laser macular photocoagulation in the treatment of diabetic macular edema. Full-thickness retinal laser burns in the areas of retinal pathology were created, visible at the time of treatment as white or gray retinal lesions ("suprathreshold" retinal photocoagulation). With time, these lesions developed into focal areas of chorioretinal scarring and progressive atrophy.

With visible endpoint photocoagulation, laser light absorption heats pigmented tissues at the laser site. Heat conduction spreads this temperature increase from the retinal pigment epithelium and choroid to overlying non-pigmented and adjacent unexposed tissues. Laser lesions become visible immediately when damaged neural retina overlying the laser sight loses its transparency and scatters white ophthalmoscopic light back towards the observer.

There are different exposure thresholds for retinal lesions that are haemorrhagic, ophthalmoscopically apparent, or angiographically demonstrable. A "threshold" lesion is one that is barely visible ophthalmoscopically at treatment time, a "subthreshold" lesion is one that is not visible at treatment time, and "suprathreshold" laser therapy is retinal photocoagulation performed to a readily visible endpoint. Traditional retinal photocoagulation treatment requires a visible endpoint either to produce a "threshold" lesion or a "suprathreshold" lesion so as to be readily visible and tracked. In fact, it has been believed that actual tissue damage and scarring are necessary in order to create the benefits of the procedure. The gray to white retinal burns testify to the thermal retinal destruction inherent in conventional threshold and suprathreshold photocoagulation. Photocoagulation has been found to be an effective means of producing retinal scars, and has become the technical standard for macular photocoagulation for diabetic macular edema for nearly 50 years.

With reference now to FIG. 1, a diagrammatic view of an eye, generally referred to by the reference number 10, is shown. When using phototherapy, the laser light is passed through the patient's cornea 12, pupil 14, and lens 16 and directed onto the retina 18. The retina 18 is a thin tissue layer which captures light and transforms it into the electrical signals for the brain. It has many blood vessels, such as those referred to by reference number 20, to nourish it. Various retinal diseases and disorders, and particularly vascular retinal diseases such as diabetic retinopathy, are treated using conventional thermal retinal photocoagulation, as discussed above. The fovea/macula region, referred to by the reference number 22 in FIG. 1, is a portion of the eye used for color vision and fine detail vision. The fovea is at the center of the macula, where the concentration of the cells needed for central vision is the highest. Although it is this area where diseases such as age-related macular degeneration are so damaging, this is the area where conventional photocoagulation phototherapy cannot be used as damaging the cells in the foveal area can significantly damage the patient's vision. Thus, with current convention photocoagulation therapies, the foveal region is avoided.

That iatrogenic retinal damage is necessary for effective laser treatment of retinal vascular disease has been universally accepted for almost five decades, and remains the prevailing notion. Although providing a clear advantage compared to no treatment, current retinal photocoagulation treatments, which produce visible gray to white retinal burns and scarring, have disadvantages and drawbacks. Conventional photocoagulation is often painful. Local anesthesia, with its own attendant risks, may be required. Alternatively, treatment may be divided into stages over an extended period of time to minimize treatment pain and post-operative inflammation. Transient reduction in visual acuity is common following conventional photocoagulation.

In fact, thermal tissue damage may be the sole source of the many potential complications of conventional photocoagulation which may lead to immediate and late visual loss. Such complications include inadvertent foveal burns, pre- and subretinal fibrosis, choroidal neovascularization, and progressive expansion of laser scars. Inflammation resulting from the tissue destruction may cause or exacerbate macular edema, induced precipitous contraction of fibrovascular proliferation with retinal detachment and vitreous hemorrhage, and cause uveitis, serous choroidal detachment, angle closure or hypotony. Some of these complications are rare, while others, including treatment pain, progressive scar expansion, visual field loss, transient visual loss and decreased night vision are so common as to be accepted as inevitable side-effects of conventional laser retinal photocoagulation. In fact, due to the retinal damage inherent in conventional photocoagulation treatment, it has been limited in density and in proximity to the fovea, where the most visually disabling diabetic macular edema occurs.

Notwithstanding the risks and drawbacks, retinal photocoagulation treatment, typically using a visible laser light, is the current standard of care for proliferative diabetic retinopathy, as well as other retinopathy and retinal diseases, including diabetic macular edema and retinal venous occlusive diseases which also respond well to retinal photocoagulation treatment. In fact, retinal photocoagulation is the current standard of care for many retinal diseases, including diabetic retinopathy.

Another problem is that the treatment requires the application of a large number of laser doses to the retina, which can be tedious and time-consuming. Typically, such treatments call for the application of each dose in the form of a laser beam spot applied to the target tissue for a predetermined amount of time, from a few hundred milliseconds to several seconds. Typically, the laser spots range from 50-500 microns in diameter. Their laser wavelength may be green, yellow, red or even infrared. It is not uncommon for hundreds or even in excess of one thousand laser spots to be necessary in order to fully treat the retina. The physician is responsible for insuring that each laser beam spot is properly positioned away from sensitive areas of the eye, such as the fovea, that could result in permanent damage. Laying down a uniform pattern is difficult and the pattern is typically more random than geometric in distribution. Point-by-point treatment of a large number of locations tends to be a lengthy procedure, which frequently results in physician fatigue and patient discomfort.

U.S. Pat. No. 6,066,128, to Bahmanyar describes a method of multi-spot laser application, in the form of retinal-destructive laser photocoagulation, achieved by means of distribution of laser irradiation through an array of multiple separate fiber optic channels and micro lenses. While overcoming the disadvantages of a point-by-point laser spot procedure, this method also has drawbacks. However, a limitation of the Bahmanyar method is differential degradation or breakage of the fiber optics or losses due to splitting the laser source into multiple fibers, which can lead to uneven, inefficient and/or suboptimal energy application. Another limitation is the constraint on the size and density of the individual laser spots inherent in the use of an optical system of light transmission fibers in micro lens systems. The mechanical constraint of dealing with fiber bundles can also lead to limitations and difficulties focusing and aiming the multi-spot array.

U.S. Patent Publication 2010/0152716 A1 to Previn describes a different system to apply destructive laser irradiation to the retina using a large retinal laser spot with a speckle pattern, oscillated at a high frequency to homogenize the laser irradiance throughout the spot. However, a problem with this method is the uneven heat buildup, with higher tissue temperatures likely to occur toward the center of the large spot. This is aggravated by uneven heat dissipation by the ocular circulation resulting in more efficient cooling towards the margins of the large spot compared to the center. That is, the speckle pattern being oscillated at a high frequency can cause the laser spots to be overlapping or so close to one another that heat builds up and undesirable tissue damage occurs. Previn's speckle technique achieves averaging of point laser exposure within the larger exposure via the random fluctuations of the speckle pattern. However, such averaging results from some point exposures being more intense than others, whereas some areas within the exposure area may end with insufficient laser exposure, whereas other areas will receive excessive laser exposure. In fact, Previn specifically notes the risk of excessive exposure or exposure of sensitive areas, such as the fovea, which should be avoided with this system. Although these excessively exposed spots may result in retinal damage, Previn's invention is explicitly intended to apply damaging retinal photocoagulation to the retina, other than the sensitive area such as the fovea.

However, all conventional retinal photocoagulation treatments, including those described by Previn and Bahmanyar, create visible endpoint laser photocoagulation in the form of gray to white retinal burns and lesions, as discussed above. Recently, the inventor has discovered that subthreshold photocoagulation in which no visible tissue damage or laser lesions were detectable by any known means including ophthalmoscopy; infrared, color, red-free or autofluorescence fundus photography in standard or retro-mode; intravenous fundus fluorescein or indocyanine green angiographically, or Spectral-domain optical coherence tomography at the time of treatment or any time thereafter has produced similar beneficial results and treatment without many of the drawbacks and complications resulting from conventional visible threshold and suprathreshold photocoagulation treatments. It has been determined that with the proper operating parameters, subthreshold photocoagulation treatment can be, and may ideally be, applied to the entire retina, including sensitive areas such as the fovea, without visible tissue damage or the resulting drawbacks or complications of conventional visible retinal photocoagulation treatments. Moreover, by desiring to treat the entire retina, or confluently treat portions of the retina, laborious and time-consuming point-by-point laser spot therapy can be avoided. In addition, the inefficiencies and inaccuracies inherent to invisible endpoint laser treatment resulting in suboptimal tissue target coverage can also be avoided.

SUMMARY OF THE INVENTION

The present invention resides in a process and system for treating retinal diseases and disorders by means of harmless, subthreshold photocoagulation phototherapy. Although the present invention is particularly useful in treating diabetic retinopathy, including diabetic macular edema, it will be understood that the present invention also applies to all other retinal conditions, including but not limited to retinal venous occlusive diseases and idiopathic central serous chorioretinopathy, proliferative diabetic retinopathy, and retinal macroaneurysm as reported, which respond well to traditional retinal photocoagulation treatments; but having potential application as preventative and rejuvenative in disorders such as genetic diseases and age-related macular degeneration and others.

In accordance with the present invention, a system for treating retinal diseases and disorders comprises a laser producing a micropulsed light beam. In a particularly preferred embodiment, the laser produces a light beam having an infrared wavelength, such as between 750 nm-1300 nm, and preferably approximately 810 nm. The light beam has an intensity of between 100-590 watts per square centimeter, and preferably approximately 350 watts per square centimeter. The pulse length of the laser is 500 milliseconds or less. The laser has a duty cycle of less than 10%, and typically approximately 5%.

An optical lens or mask optically shapes the light beam from the laser into a geometric object or pattern. For example, the optical lens or mask, such as a diffraction grating, produces a simultaneous pattern of spaced apart laser spots.

An optical scanning mechanism controllably directs the light beam object or pattern onto the retina. The light beam geometric object or pattern is incrementally moved a sufficient distance from where the light beam was previously applied to the retina, to avoid tissue damage, prior to reapplying the light beam to the retina.

The light beam is applied to at least a portion of the retina, such as at eighteen to fifty-five times the American National Standards Institute (ANSI) maximum permissible exposure (MPE) level. Given the parameters of the generated laser light beam, including the pulse length, power, and duty cycle, no visible laser lesions or tissue damage is detectable ophthalmoscopiCally or angiographically after treatment, allowing the entire retina, including the fovea, to be treated without damaging retinal or foveal tissue while still providing the benefits of photocoagulation treatment.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIGS. 2A-2F are graphic representations of the effective surface area of various modes of retinal laser treatment;

DETAILED DESCRIPTION OF THE PREFERRED EMBODIMENTS

Figure 1:
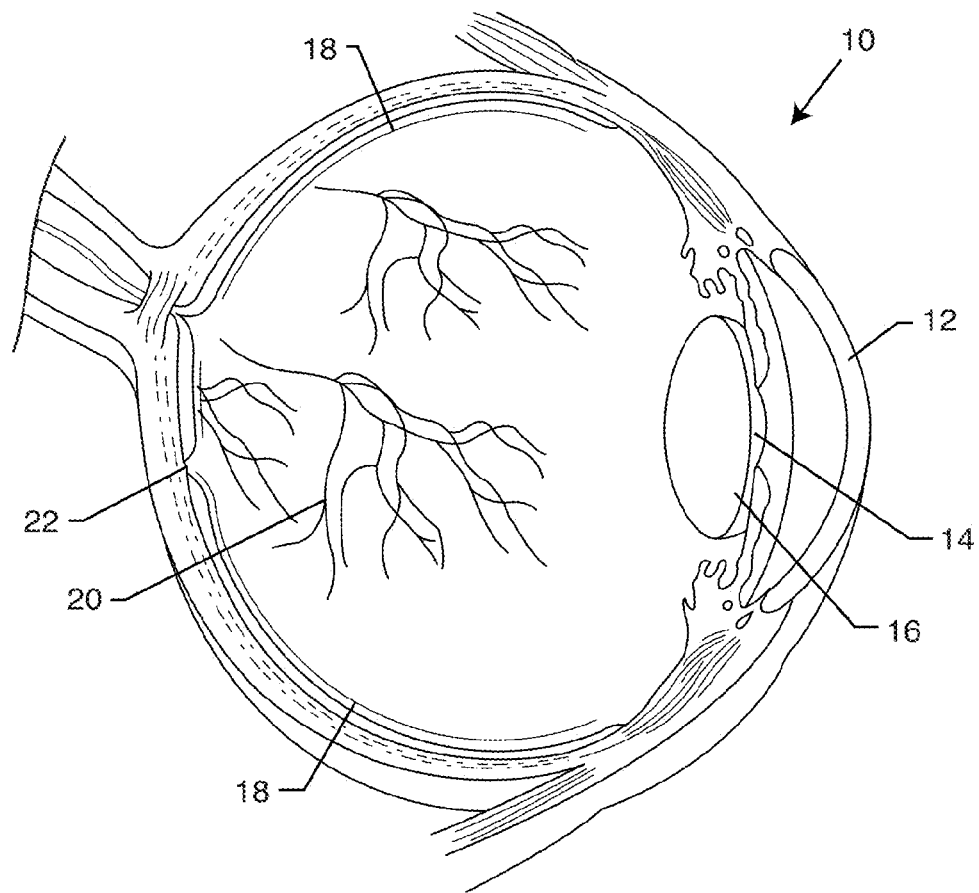
FIG. 1 is a cross-sectional diagrammatic view of a human eye.

The present invention relates to a system and process for treating retinal diseases, including vascular retinal diseases such as diabetic retinopathy and diabetic macular edema, by means of predetermined parameters producing harmless, true subthreshold photocoagulation. The inventor's finding that retinal laser treatment that does not cause any laser-induced retinal damage, but can be at least as effective as conventional retinal photocoagulation is contrary to conventional thinking and practice.

Conventional thinking assumes that the physician must intentionally create retinal damage as a prerequisite to therapeutically effective treatment. With reference to FIG. 2, FIGS. 2A-2F are graphic representations of the effective surface area of various modes of retinal laser treatment for retinal vascular disease. The gray background represents the retina 30 which is unaffected by the laser treatment. The black areas 32 are areas of the retina which are destroyed by conventional laser techniques. The lighter gray or white areas 34 represent the areas of the retina affected by the laser, but not destroyed.

FIG. 2A illustrates the therapeutic effect of conventional argon laser retinal photocoagulation. The therapeutic effects attributed to laser-induced thermal retinal destruction include reduced metabolic demand, debulking of diseased retina, increased intraocular oxygen tension and ultra production of vasoactive cytokines, including vascular endothelial growth factor (VEGF).

With reference to FIG. 2B, increasing the burn intensity of the traditional laser burn is shown. It will be seen that the burned and damaged tissue area 32 is larger, which has resulted in a larger "halo effect" of heated, but undamaged, surrounding tissue 34. Laboratory studies have shown that increased burn intensity is associated with an enhanced therapeutic effect, but hampered by increased loss of functional retina inflammation. However, with reference to FIG. 2C, when the intensity of the conventional argon laser photocoagulation is reduced, the area of the retina 34 affected by the laser but not destroyed is also reduced, which may explain the inferior clinical results from lower-intensity/lower-density or "mild" argon laser grid photocoagulation compared to higher-intensity/higher-density treatment, as illustrated in FIG. 2B.

With reference to FIG. 2D, it has been found that low-fluence photocoagulation with short-pulse continuous wave laser photocoagulation, also known as selective retinal therapy, produces minimal optical and lateral spread of laser photothermal tissue effects, to the extent that the area of the retina affected by the laser but not destroyed is minimal to nonexistent. Thus, despite complete oblation of the directly treated retina 30, the rim of the therapeutically affected and surviving tissue is scant or absent. This explains the recent reports finding superiority of conventional argon laser photocoagulation over PASCAL for diabetic retinopathy.

However, the inventor has questioned whether such thermal retinal damage is necessary, and whether it accounts for the benefits of the conventional laser treatments. Instead, the inventor has surmised that the therapeutic alterations in the retinal pigment epithelium (RPE) cytokine production elicited by conventional photocoagulation comes from cells at the margins of traditional laser burns, affected but not killed by the laser exposure, referred to by the reference number 34 in FIG. 2.

FIG. 2E represents the use of a low-intensity and low-density micropulsed laser, such as a micropulsed diode laser. This creates subthreshold retinal photocoagulation, shown by the reference number 34, without any visible burn areas 32. All areas of the retinal pigment epithelium exposed to the laser irradiation are preserved, and available to contribute therapeutically.

The subthreshold retinal photocoagulation is defined as retinal laser applications biomicroscopically invisible at the time of treatment. Unfortunately, the term has often been used in the art to describe several different clinical scenarios reflecting widely varying degrees of laser-induced thermal retinal damage. The use of the term "subthreshold" falls into three categories reflecting common usage and the historical and morphological evolution of reduced-intensity photocoagulation for retinal vascular disease toward truly invisible phototherapy which the invention embodies.

"Classical subthreshold" for photocoagulation describes the early attempts at laser intensity reduction using conventional continuous argon, krypton, and diode lasers. Although the retinal burns were notably less obvious than the conventional "threshold" (photocoagulation confined to the outer retina and thus less visible at time of treatment) or even milder "suprathreshold" (full-thickness retinal photocoagulation generally easily visible at the time of treatment), the lesions of "classical" subthreshold photocoagulation were uniformly visible both clinically and by fundus fluorescein angiography (FFA) at the time of treatment and thereafter.

"Clinical subthreshold" photocoagulation describes the next epiphany of evolution of laser-induced retinal damage reduction, describing a lower-intensity but persistently damaging retinal photocoagulation using either a micropulsed laser or short-pulsed continuous wave laser that better confine the damage to the outer retina and retinal pigmentation epithelium. In "clinical" subthreshold photocoagulation, the laser lesions may in fact be ophthalmoscopically invisible at the time of treatment, however, as laser-induced retinal damage remains the intended point of treatment, laser lesions are produced which generally become increasingly clinically visible with time, and many, if not all, laser lesions can be seen by FFA, fundus autofluorescence photography (FAF), and/or spectral-domain (SD) optical coherence tomography (OCT) at the time of treatment and thereafter.

"True" subthreshold photocoagulation, as a result of the present invention, is invisible and includes laser treatment non-discernable by any other known means such as FFA, FAF, or even SD-OCT. "True subthreshold" photocoagulation is therefore defined as a laser treatment which produces absolutely no retinal damage detectable by any means at the time of treatment or any time thereafter by known means of detection. As such, with the absence of lesions and other tissue damage and destruction, FIGS. 2E and 2F represent the result of "true", invisible subthreshold photocoagulation.

Various parameters have been determined to achieve "true" subthreshold or "low-intensity" effective photocoagulation. These include providing sufficient power to produce effective treatment retinal laser exposure, but not too high to create tissue damage or destruction. True subthreshold laser applications can be applied singly or to create a geometric object or pattern of any size and configuration to minimize heat accumulation, but assure uniform heat distribution as well as maximizing heat dissipation, and using a low duty cycle. The inventor has discovered how to achieve therapeutically effective and harmless true subthreshold retinal laser treatment. The inventor has also discovered that placement of true subthreshold laser applications confluently and contiguously to the retinal surface improves and maximizes the therapeutic benefits of treatment without harm or retinal damage.

The American Standards Institute (ANSI) has developed standards for safe workplace laser exposure based on the combination of theoretical and empirical data. The "maximum permissible exposure" (MPE) is the safety level, set at approximately 1/10th of the laser exposure level expected to produce biological effects. At a laser exposure level of 1 times MPE, absolute safety would be expected and retinal exposure to laser radiation at this level would be expected to have no biologic affect. Based on ANSI data, a 50% of some risk of suffering a barely visible (threshold) retinal burn is generally encountered at 10 times MPE for conventional continuous wave laser exposure. For a low-duty cycle micropulsed laser exposure of the same power, the risk of threshold retinal burn is approximately 100 times MPE. Thus, the therapeutic range—the interval of doing nothing at all and the 50% of some likelihood of producing a threshold retinal burn—for low-duty cycle micropulsed laser irradiation is 10 times wider than for continuous wave laser irradiation with the same energy. It has been determined that safe and effective subthreshold photocoagulation using a micropulsed diode laser is between 18 times and 55 times MPE, with a preferred laser exposure to the retina at 47 times RPE for a near-infrared 810 nm diode laser. At this level, the inventor has observed that there is therapeutic effectiveness with no discernible retinal damage whatsoever.

It has been found that the intensity or power of a laser beam between 100 watts to 590 watts per square centimeter is effective yet safe. A particularly preferred intensity or power of the laser light beam is approximately 350 watts per square centimeter for an 810 nm micropulsed diode laser.

Power limitations in current micropulsed diode lasers require fairly long exposure duration. The longer the laser exposure, the more important the center-spot heat dissipating ability toward the unexposed tissue at the margins of the laser spot and toward the underlying choriocapillaris. Thus, the micropulsed laser light beam of an 810 nm diode laser should have an exposure envelope duration of 500 milliseconds or less, and preferably approximately 300 milliseconds. Of course, if micropulsed diode lasers become more powerful, the exposure duration will be lessened accordingly.

Another parameter of the present invention is the duty cycle (the frequency of the train of micropulses, or the length of the thermal relaxation time in between consecutive pulses). It has been found that the use of a 10% duty cycle or higher adjusted to deliver micropulsed laser at similar irradiance at similar MPE levels significantly increase the risk of lethal cell injury, particularly in darker fundi. However, duty cycles less than 10%, and preferably approximately 5% duty cycle (or less) demonstrated adequate thermal rise and treatment at the level of the MPE cell to stimulate a biologic response, but remained below the level expected to produce lethal cell injury, even in darkly pigmented fundi. Moreover, if the duty cycle is less than 5%, the exposure envelope duration in some instances can exceed 500 milliseconds.

In a particularly preferred embodiment, the use of small retinal laser spots is used. This is due to the fact that larger spots can contribute to uneven heat distribution and insufficient heat dissipation within the large retinal laser spot, potentially causing tissue damage or even tissue destruction towards the center of the larger laser spot. In this usage, "small" would generally apply to retinal spots less than 1 mm in diameter. However, the smaller the retinal spot, the more ideal the heat dissipation and uniform energy application becomes. Thus, at the power intensity and exposure duration described above, small spots, such as along the size of the wavelength of the laser, or small geometric lines or other objects are preferred so as to maximize even heat distribution and heat dissipation to avoid tissue damage.

Thus, the following key parameters have been found in order to create harmless, "true" subthreshold photocoagulation in accordance with the present invention: a) a low (preferably 5% or less) duty cycle; b) a small spot size to minimize heat accumulation and assure uniform heat distribution within a given laser spot so as to maximize heat dissipation; c) sufficient power to produce retinal laser exposures of between 18 times-55 times MPE producing an RPE temperature rise of 7° C.-14° C.; and retinal irradiance of between 100-590 W/cm$^2$.

Using the foregoing parameters, a harmless, "true" subthreshold photocoagulation phototherapy treatment can be attained which has been found to produce the benefits of conventional photocoagulation phototherapy, but avoid the drawbacks and complications of conventional phototherapy. In fact, "true" subthreshold photocoagulation phototherapy in accordance with the present invention enables the physician to apply a "low-intensity/high-density" phototherapy treatment, such as illustrated in FIG. 2F, and treat the entire retina, including sensitive areas such as the macula and even the fovea without creating visual loss or other damage. As indicated above, using conventional phototherapies, the entire retina, and particularly the fovea, cannot be treated as it will create vision loss due to the tissue damage in sensitive areas.

Conventional retina-damaging laser treatment is limited in treatment density, requiring subtotal treatment of the retina, including subtotal treatment of the particular areas of retinal abnormality. However, recent studies demonstrate that eyes in diabetics may have diffuse retinal abnormalities without otherwise clinically visible diabetic retinopathy, and eyes with localized areas of clinically identifiable abnormality, such as diabetic macular edema or central serous chorioretinopathy, often have total retinal dysfunction detectable only by retinal function testing. The ability of the invention to harmlessly treat the entire retina thus allows, for the first time, both preventative and therapeutic treatment of eyes with retinal disease completely rather than locally or subtotally; and early treatment prior to the manifestation of clinical retinal disease and visual loss.

As discussed above, it is conventional thinking that tissue damage and lesions must be created in order to have a therapeutic effect. However, the invention has found that this simply is not the case. In the absence of laser-induced retinal damage, there is no loss of functional retinal tissue and no inflammatory response to treatment. Adverse treatment effects are thus completely eliminated and functional retina preserved rather than sacrificed. This may yield superior visual acuity results compared to conventional photocoagulation treatment.

The present invention spares the neurosensory retina and is selectively absorbed by the RPE. Current theories of the pathogenesis of retinal vascular disease especially implicate cytokines, potent extra cellular vasoactive factors produced by the RPE, as important mediators of retinal vascular disease. The present invention both selectively targets and avoids lethal buildup within RPE. Thus, with the present invention the capacity for the treated RPE to participate in a therapeutic response is preserved and even enhanced rather than eliminated as a result their destruction of the RPE in conventional photocoagulation therapies.

It has been noted that the clinical effects of cytokines may follow a "U-shaped curve" where small physiologic changes in cytokine production, denoted by the left side of curve, may have large clinical effects comparable to high-dose (pharmacologic) therapy (denoted by the right side of the curve). Using sublethal laser exposures in accordance with the present invention may be working on the left side of the curve where the treatment response may approximate more of an "on/off" phenomenon rather than a dose-response. This might explain the clinical effectiveness of the present invention observed at low reported irradiances. This is also consistent with clinical experience and in-vitro studies of laser-tissue interaction, wherein increasing irradiance may simply increase the risk of thermal retinal damage without improving the therapeutic effect.

With reference again to FIG. 2, the invisible, true sub-threshold photocoagulation phototherapy maximizes the therapeutic recruitment of the RPE through the concept of "maximize the affected surface area", in that all areas of RPE exposed to the laser irradiation are preserved, and available to contribute therapeutically. As discussed above with respect to FIG. 2, it is believed that conventional therapy creates a therapeutic ring around the burned or damaged tissue areas, whereas the present invention creates a therapeutic area without any burned or otherwise destroyed tissue.

In another departure from conventional retinal photocoagulation, a low red to infrared laser light beam, such as from an 810 nm micropulsed diode laser, is used instead of an argon laser. It has been found that the 810 nm diode laser is minimally absorbed and negligibly scattered by intraretinal blood, cataract, vitreous hemorrhage and even severely edematous neurosensory retina. Differences in fundus coloration result primarily from differences in choroid pigmentation, and less of variation of the target RPE. Treatment in accordance with the present invention is thus simplified, requiring no adjustment in laser parameters for variations in macular thickening, intraretinal hemorrhage, mediaopacity or fundus pigmentation, reducing the risk of error.

However, it is contemplated that the present invention could be utilized with micropulsed emissions of shorter wavelengths, such as the recently available 577 nm yellow and 532 nm green lasers. The higher energies and different tissue absorption characteristic of shorter wavelength lasers may increase retinal burn risk, effectively narrowing the therapeutic window. In addition, the shorter wavelengths are more scattered by opaque ocular media, retinal hemorrhage and macular edema, potentially limiting usefulness and increasing the risk of retinal damage in certain clinical settings. Thus, a low red to infrared laser light beam is still preferred.

In fact, low power red and near-infrared laser exposure is known to affect many cell types, particularly altering the behavior of cells and pathological environments, such as diabetes, through a variety of intracellular photoreceptors. Cell function, in cytokine expression, is normalized and inflammation reduced. By normalizing function of the viable RPE cells, the invention may induce changes in the expression of multiple factors physiologically as opposed to drug therapy that typically narrowly targets only a few post-cellular factors pharmacologically. The laser-induced physiologic alteration of RPE cytokine expression may account for the slower onset but long lasting benefits using the present invention. Furthermore, use of a physiologically invisible infrared or near-infrared laser wavelength is perceived as comfortable by the patient, and does not cause reactive pupillary constriction, allowing visualization of the ocular fundus and treatment of the retina to be performed without pharmacologic dilation of the patient pupil. This also eliminates the temporary of visual disability typically lasting many hours following pharmacologic pupillary dilation currently required for treatment with conventional laser photocoagulation. Currently, patient eye movement is a concern not only for creating the pattern of laser spots to treat the intended area, but also could result in exposure of conventional therapy to sensitive areas of the eye, such as the fovea, resulting in loss of vision or other complications.

Figure 3:
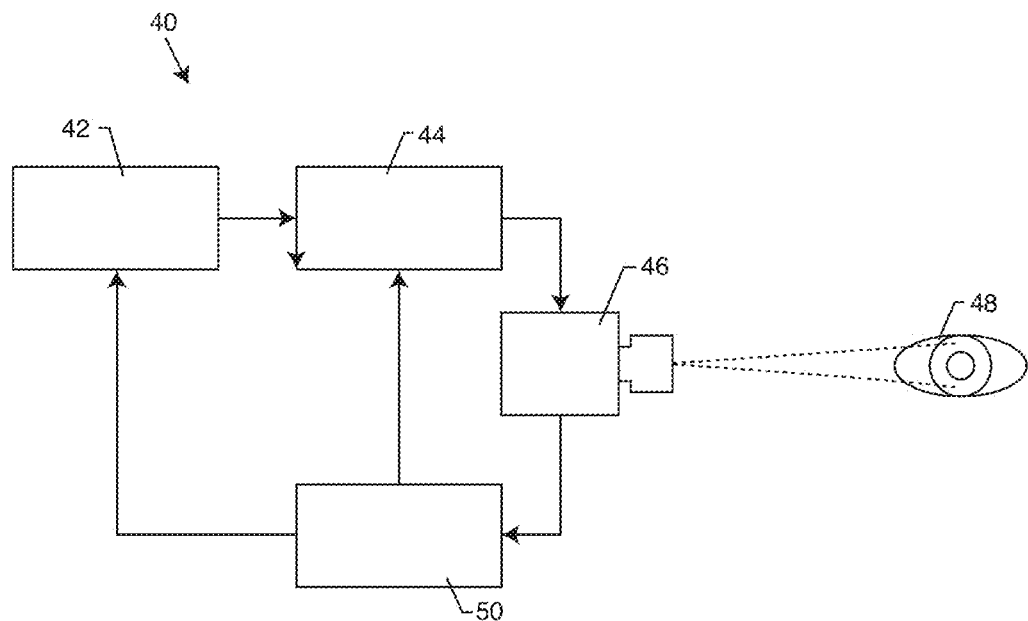
FIG. 3 is a diagrammatic view illustrating a system used for treating a retinal disease or disorder in accordance with the present invention.

With reference now to FIG. 3, a schematic diagram is shown of a system for realizing the process of the present invention. The system, generally referred to by the reference number 40, includes a laser console 42, such as for example the 810 nm near infrared micropulsed diode laser in the preferred embodiment. The laser generates a laser light beam which is passed through an optical lens or mask, or a plurality of optical lenses and/or masks 44 as needed. The laser projector optics 44 pass the shaped light beam to a coaxial wide-field non-contact digital optical viewing system/camera 46 for projecting the laser beam light onto the eye 48 of the patient. It will be understood that the box labeled 46 can represent both the laser beam projector as well as a viewing system/camera, which might in reality comprise two different components in use. The viewing system/camera 46 provides feedback to a display monitor 50, which may also include the necessary computerized hardware, data input and controls, etc. for manipulating the laser 42, the optics 44, and/or the projection/viewing components 46.

As discussed above, current treatment requires the application of a large number of individual laser beam spots applied to the target tissue to be treated. These can number in the hundreds or even thousands for the desired treatment area. This is very time intensive and laborious.

Figure 4:
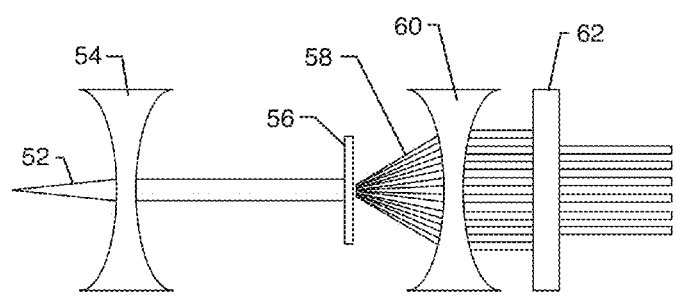
FIG. 4 is a diagrammatic view of an exemplary optical lens or mask used to generate a geometric pattern, in accordance with the present invention.

With reference now to FIG. 4, in one embodiment, the laser light beam 52 is passed through a collimater lens 54 and then through a mask 56. In a particularly preferred embodiment, the mask 56 comprises a diffraction grating. The mask/diffraction grating 56 produces a geometric object, or more typically a geometric pattern of simultaneously produced multiple laser spots or other geometric objects. This is represented by the multiple laser light beams labeled with reference number 58. Using diffraction gratings or other diffraction optics allows use of a very low power lasers to drive the system of the present invention. This allows the creation of a very large number of laser spots simultaneously over a very wide treatment field, such as consisting of the entire retina. In fact, a very high number of laser spots, perhaps numbering in the thousands or even ten thousand or more could cover the entire ocular fundus and entire retina, including the macula and fovea, retinal blood vessels and optic nerve. The intent of the process in the present invention is to better ensure complete and total coverage and treatment, sparing none of the retina by the laser so as to improve vision.

Using a diffraction apertures of a size on par with the wavelength of the laser employed, it is possible to take advantage of quantum mechanical effects which significantly increases the output irradiance, and permits simultaneous application of very large number of simultaneously applied laser spots for a very large target area driven by very low power input laser. The individual spots produced by such diffraction gratings can be smaller in the order of magnitudes, with such small spot sizes having not been employed in the treatment of the retina previously. Of course, such small sizes minimize the risk of single-spot heat damage due to their small size and due to the spacing of the small spots allow heat diffusion readily. However, the present invention also contemplates the use of conventionally sized (50-500 µm) generated individual spots as well as other geometric objects and patterns.

The laser light passing through the mask 56 diffracts, producing a periodic pattern a distance away from the mask 56, shown by the laser beams labeled 58 in FIG. 4. The single laser beam 52 has thus been formed into hundreds or thousands or even tens of thousands of individual laser beams 58 so as to create the desired pattern of spots or other geometric objects. These laser beams 58 may be passed through additional lenses, collimaters, etc. 60 and 62 in order to convey the laser beams and form the desired pattern on the patient's retina. Such additional lenses, collimaters, etc. 60 and 62 can further transform and redirect the laser beams 58 as needed.

Arbitrary patterns can be constructed by controlling the shape, spacing and pattern of the optical mask 56. The pattern and exposure spots can be created and modified arbitrarily as desired according to application requirements by experts in the field of optical engineering. Photolithographic techniques, especially those developed in the field of semiconductor manufacturing, can be used to create the simultaneous geometric pattern of spots or other objects.

Typically, the system of the present invention incorporates a guidance system to ensure complete and total retinal treatment with retinal photostimulation. As the treatment method of the present invention is harmless, the entire retina, including the fovea and even optical nerve, can be treated. Moreover, protection against accidental visual loss by accidental patient movement is not a concern. Instead, patient movement would mainly affect the guidance in tracking of the application of the laser light to ensure adequate coverage. Fixation/tracking/registration systems consisting of a fixation target, tracking mechanism, and linked to system operation are common in many ophthalmic diagnostic systems and can be incorporated into the present invention.

Figure 5:
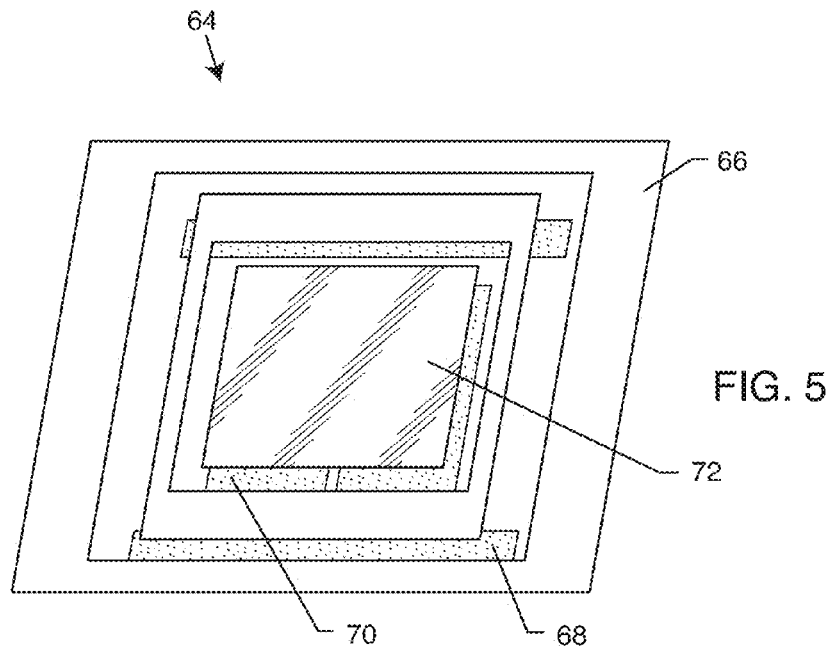
FIG. 5 is a top plan view of an optical scanning mechanism, used in accordance with the present invention.
Figure 6:
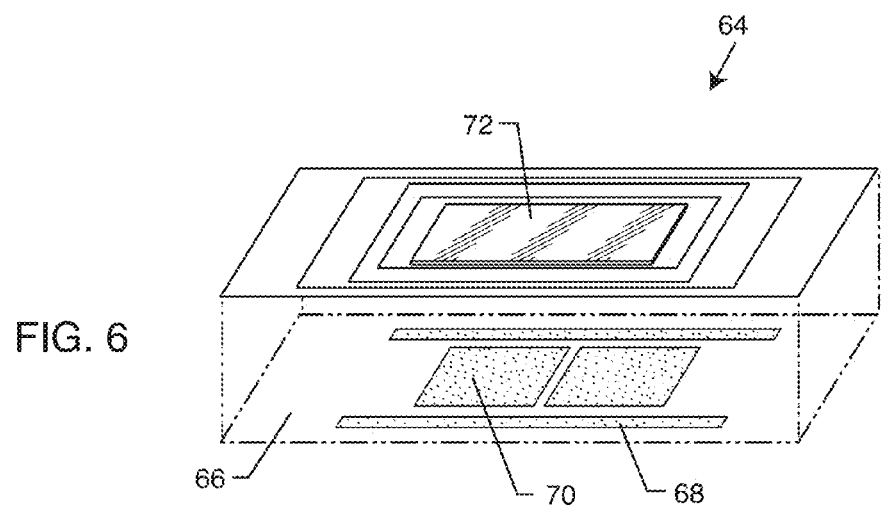
FIG. 6 is a partially exploded view of the optical scanning mechanism of FIG. 5, illustrating the various component parts thereof.

With reference now to FIGS. 5 and 6, in a particularly preferred embodiment, the geometric pattern of simultaneous laser spots is sequentially offset so as to achieve confluent and complete treatment of the retinal surface. Although a segment of the retina can be treated in accordance with the present invention, more typically the entire retina will be treated with one treatment. This is done in a time-saving manner by placing thousands of spots over the entire ocular fundus at once. This pattern of spots is scanned, shifted, or redirected as an entire array simultaneously, so as to cover the entire retina.

This can be done in a controlled manner using an optical scanning mechanism 64 such as that illustrated in FIGS. 5 and 6. FIGS. 5 and 6 illustrate an optical scanning mechanism 64 in the form of a MEMS mirror, having a base 66 with electronically actuated controllers 68 and 70 which serve to tilt and pan the mirror 72 as electricity is applied and removed thereto. Applying electricity to the controller 68 and 70 causes the mirror 72 to move, and thus the simultaneous pattern of laser spots or other geometric objects reflected thereon to move accordingly on the retina of the patient. This can be done, for example, in an automated fashion using electronic software program to adjust the optical scanning mechanism 64 until complete coverage of the retina, or at least the portion of the retina desired to be treated, is exposed to the phototherapy.

Figure 7:
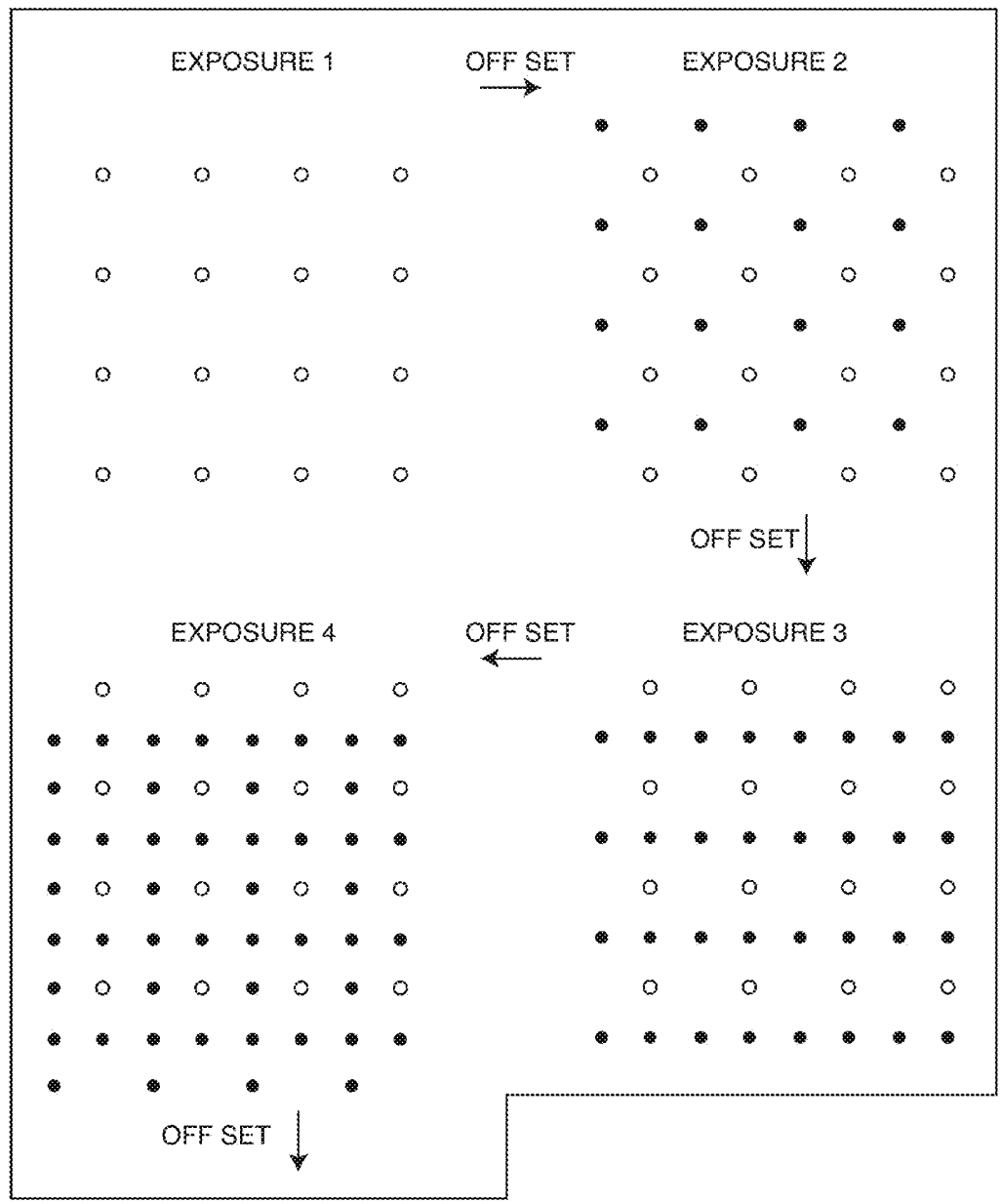
FIG. 7 illustrates controlled offset of exposure of an exemplary geometric pattern grid of laser spots to treat the retina in accordance with the present invention.

Since the parameters of the present invention dictate that the applied laser light is not destructive or damaging, the geometric pattern of laser spots, for example, can be overlapped without creating any damage. However, in a particularly preferred embodiment, as illustrated in FIG. 7, the pattern of spots are offset at each exposure so as to create space between the immediately previous exposure to allow heat dissipation and prevent the possibility of heat damage or tissue destruction. Thus, as illustrated in FIG. 7, the pattern, illustrated for exemplary purposes as a grid of sixteen spots, is offset each exposure such that the laser spots occupy a different space than previous exposures. It will be understood that this occurs until the entire retina, the preferred methodology, has received phototherapy, or until the desired effect is attained. This can be done, for example, by applying electrostatic torque to a micromachined mirror, as illustrated in FIGS. 5 and 6. By combining the use of small retina laser spots separated by exposure free areas, prevents heat accumulation, and grids with a large number of spots per side, it is possible to atraumatically and invisibly treat large target areas with short exposure durations far more rapidly than is possible with current technologies.

By rapidly and sequentially repeating redirection or offsetting of the entire simultaneously applied grid array of spots or geometric objects, complete coverage of the target, such as a human retina, can be achieved rapidly without thermal tissue injury. This offsetting can be determined algorithmically to ensure the fastest treatment time and least risk of damage due to thermal tissue, depending on laser parameters and desired application. The following has been modeled using the Fraunhoffer Approximation. With a mask having a nine by nine square lattice, with an aperture radius 9 µm, an aperture spacing of 600 µm, using a 890 nm wavelength laser, with a mask-lens separation of 75 mm, and secondary mask size of 2.5 mm by 2.5 mm, the following parameters will yield a grid having nineteen spots per side separated by 133 µm with a spot size radius of 6 µm. The number of exposures "m" required to treat (cover confluently with small spot applications) given desired area side-length "A", given output pattern spots per square side "n", separation between spots "R", spot radius "r" and desired square side length to treat area "A", can be given by the following formula:

$$m = \frac{A}{nR} \text{floor}\left(\frac{R}{2r}\right)^2.$$

With the foregoing setup, one can calculate the number of operations m needed to treat different field areas of exposure. For example, a 3 mm×3 mm area, which is useful for treatments, would require 98 offsetting operations, requiring a treatment time of approximately thirty seconds. Another example would be a 3 cm×3 cm area, representing the entire human retinal surface. For such a large treatment area, a much larger secondary mask size of 25 mm by 25 mm could be used, yielding a treatment grid of 190 spots per side separated by 133 μm with a spot size radius of 6 μm. Since the secondary mask size was increased by the same factor as the desired treatment area, the number of offsetting operations of approximately 98, and thus treatment time of approximately thirty seconds, is constant. These treatment times represent at least ten to thirty times reduction in treatment times compared to current methods of sequential individual laser spot applications. Field sizes of 3 mm would, for example, allow treatment of the entire human macula in a single exposure, useful for treatment of common blinding conditions such as diabetic macular edema and age-related macular degeneration. Performing the entire 98 sequential offsettings would ensure entire coverage of the macula.

Of course, the number and size of retinal spots produced in a simultaneous pattern array can be easily and highly varied such that the number of sequential offsetting operations required to complete treatment can be easily adjusted depending on the therapeutic requirements of the given application.

Furthermore, by virtue of the small apertures employed in the diffraction grading or mask, quantum effects such as constructive interference may be observed which magnify the input irradiance. This would allow use of relatively low power in widely available source input lasers, and allow therapeutically effective low-duty cycle diode laser micropulsed retinal irradiation, such as 350 watts per centimeter squared known to be safe and effective, over a treatment field of novel size, such as the 1.2 cm area to accomplish whole-retinal treatment.

Figure 8:
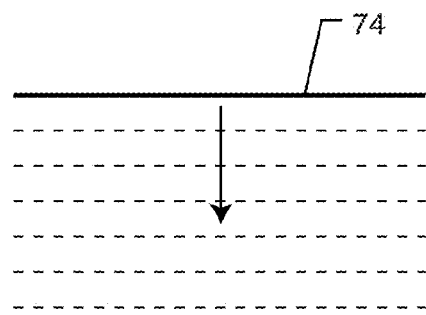
FIG. 8 is a diagrammatic view illustrating the units of a geometric object in the form of a line controllably scanned to treat an area of the retina in accordance with the present invention.

With reference now to FIG. 8, instead of a geometric pattern of small laser spots, the present invention contemplates use of other geometric objects or patterns. For example, a single line 74 of laser light, formed by the continuously or by means of a series of closely spaced spots, can be created. An offsetting optical scanning mechanism can be used to sequentially scan the line over an area, illustrated by the downward arrow in FIG. 8.

Figure 9:
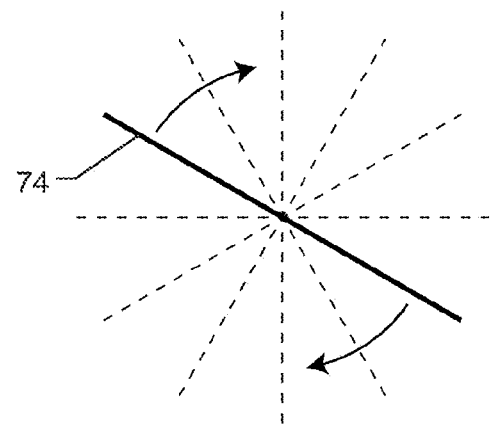
FIG. 9 is a diagrammatic view similar to FIG. 8, but illustrating the geometric line or bar rotated to treat an area of the retina.

With reference now to FIG. 9, the same geometric object of a line 74 can be rotated, as illustrated by the arrows, so as to create a circular field of phototherapy. The potential negative of this approach, however, is that the central area will be repeatedly exposed, and could reach unacceptable temperatures. This could be overcome, however, by increasing the time between exposures, or creating a gap in the line such that the central area is not exposed.

With reference again to FIG. 3, due to the unique characteristics of the present invention, allowing a single set of optimized laser parameters, which are not significantly influenced by media opacity, retinal thickening, or fundus pigmentation, a simplified user interface is permitted. While the operating controls could be presented and function in many different ways, the system permits a very simplified user interface that might employ only two control functions. That is, an "activate" button, wherein a single depression of this button while in "standby" would actuate and initiate treatment. A depression of this button during treatment would allow for premature halting of the treatment, and a return to "standby" mode. The activity of the machine could be identified and displayed, such as by an LED adjacent to or within the button. A second controlled function could be a "field size" knob. A single depression of this button could program the unit to produce, for example, a 3 mm focal or a "macular" field spot. A second depression of this knob could program the unit to produce a 6 mm or "posterior pole" spot. A third depression of this knob could program the unit to produce a "pan retinal" or approximately 160°-220° panoramic retinal spot or coverage area. Manual turning of this knob could produce various spot field sizes therebetween. Within each field size, the density and intensity of treatment would be identical. Variation of the field size would be produced by optical or mechanical masking or apertures.

The laser could be projected via a wide field non-contact lens to the ocular fundus. Customized direction of the laser fields or particular target or area of the ocular fundus other than the central area could be accomplished by an operator joy stick or eccentric patient gaze. The laser delivery optics could be coupled coaxially to a wide field non-contact digital ocular fundus viewing system. The image of the ocular fundus produced could be displayed on a video monitor visible to the laser operator. Maintenance of a clear and focused image of the ocular fundus could be facilitated by a joy stick on the camera assembly manually directed by the operator. Alternatively, addition of a target registration and tracking system to the camera software would result in a completely automated treatment system.

A fixation image could be coaxially displayed to the patient to facilitate ocular alignment. This image would change in shape and size, color, intensity, blink or oscillation rate or other regular or continuous modification during treatment to avoid photoreceptor exhaustion, patient fatigue and facilitate good fixation.

Fixation software could monitor the displayed image of the ocular fundus. Prior to initiating treatment of a fundus landmark, such as the optic nerve, or any part or feature of either eye of the patient (assuming orthophoria), could be marked by the operator on the display screen. Treatment could be initiated and the software would monitor the fundus image or any other image-registered to any part of either eye of the patient (assuming orthophoria) to ensure adequate fixation. A break in fixation would automatically interrupt treatment. Treatment would automatically resume toward completion as soon as fixation was established. At the conclusion of treatment, determined by completion of confluent delivery of the desired laser energy to the target, the unit would automatically terminate exposure and default to the "on" or "standby" mode. Due to unique properties of this treatment, fixation interruption would not cause harm or risk patient injury, but only prolong the treatment session.

Figure 10:
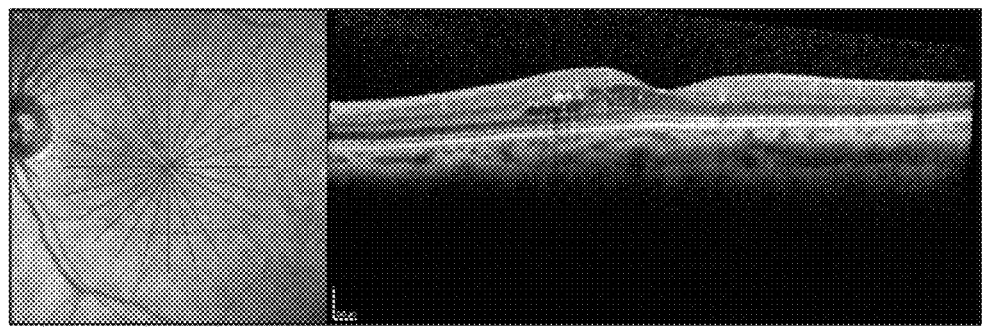
FIG. 10 is an illustration of a cross-sectional view of a diseased human retina before treatment with the present invention.
Figure 11:
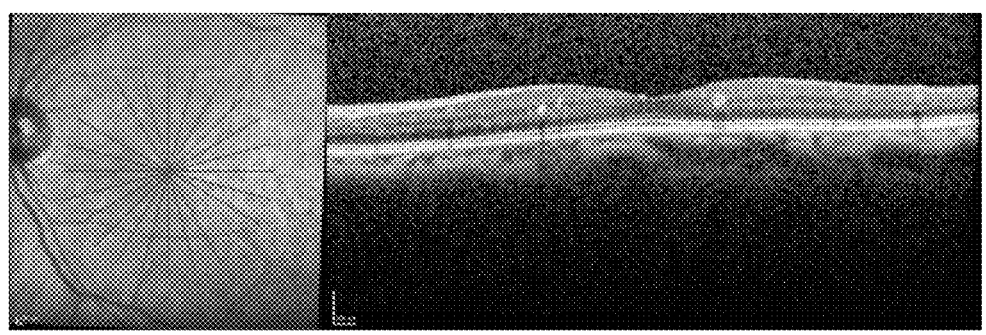
FIG. 11 is a cross-sectional view similar to FIG. 10, illustrating the portion of the retina after treatment using the present invention.

With reference now to FIGS. 10 and 11, spectral-domain OCT imaging is shown in FIG. 10 of the macular and foveal area of the retina before treatment with the present invention. FIG. 11 is of the optical coherence tomography (OCT) image of the same macula and fovea after treatment using the present invention, using a 131 micrometer retinal spot, 5% duty cycle, 0.3 second pulse duration, 0.9 watt power placed throughout the area of macular thickening, including the fovea. It will be noted that the enlarged dark area to the left of the fovea depression (representing the pathologic retinal thickening of diabetic macular edema) is absent, as well as the fact that there is an absence of any laser-induced retinal damage. Such treatment simply would not be attainable with conventional techniques.

Although the present invention is particularly suited for treatment of vascular retinal diseases, such as diabetic retinopathy and macular edema, it is contemplated that it could be used for other diseases as well. The system and process of the present invention could target the trabecular mesh work as treatment for glaucoma, accomplished by another customized treatment field template. It is contemplated by the present invention that the system and concepts of the present invention be applied to phototherapy treatment of other tissues, such as, but not limited to, the gastrointestinal or respiratory mucosa, delivered endoscopically, for other purposes.

Although several embodiments have been described in detail for purposes of illustration, various modifications may be made without departing from the scope and spirit of the invention. Accordingly, the invention is not to be limited, except as by the appended claims.

What is claimed is:

1. A process for treating a retinal disease or disorder, comprising the steps of:
    generating a micropulsed laser light beam having a wavelength greater than 532 nm and a duty cycle of less than 10% so as to create harmless, subthreshold photocoagulation when the laser light beam is applied to retinal and foveal tissue;
    passing the light beam through an optical lens or mask to optically shape the light beam and simultaneously generate a plurality of spaced apart treatment laser light spots; and
    applying the light beam, comprising the plurality of spaced apart treatment light spots, to at least a portion of the retina, including at least a portion of the fovea, without damaging retinal or foveal tissue.

2. The process of claim 1, wherein the intensity of the laser light beam is 100-590 watts per square centimeter.

3. The process of claim 2, wherein the intensity of the laser light beam is approximately 350 watts per square centimeter.

4. The process of claim 1, including the step of applying the laser light beam to the retina at 18 to 55 times the American National Standards Institute Maximum Permissible Exposure level.

5. The process of claim 1, including the step of applying the laser light beam to substantially the entire retina and fovea.

6. The process of any of claims 1-5, including the step of shaping the light beam to a geometric object or pattern.

7. The process of claim 6, including the step of controllably moving the geometric object or pattern to treat adjacent retinal tissue.

8. The process of claim 7, wherein the moving step includes the steps of incrementally moving the light beam geometric object or pattern a sufficient distance from where the light beam was previously applied to the retina, to avoid thermal tissue damage, prior to reapplying the light beam to the retina.

9. The process of any of claims 1-5, wherein the laser light beam has a wavelength between 750 nm-1300 nm.

10. The process of claim 9, wherein the laser light beam has a wavelength of approximately 810 nm.

11. The process of claim 1, wherein the micropulsed laser light beam has a duty cycle of approximately 5% or less.

12. The process of any of claims 1-5, wherein generating step includes the step of generating a micropulsed laser light beam having a pulse length of 500 milliseconds or less.

13. The process of claim 1, wherein true subthreshold phototherapy is achieved.

14. A process for treating a retinal disease or disorder, comprising the steps of:
    generating a micropulsed laser light beam having a duty cycle of 5% or less, a wavelength of between 750 nm-1,300 nm, and a power and pulse length to create harmless, subthreshold photocoagulation when the light beam is applied to retinal or foveal tissue;
    creating a geometric object or pattern of a plurality of simultaneously generated and spaced apart treatment light spots from the light beam; and
    applying the light beam geometric object or pattern to the retina for 500 milliseconds or less;
    controllably moving the light beam geometric object or pattern until substantially the entire retina, including the fovea, has been exposed to the light beam without damaging retinal or foveal tissue.

15. The process of claim 14, wherein the moving step includes the steps of incrementally moving the light beam geometric object or pattern a sufficient distance from where the light beam was previously applied to the retina, to avoid thermal tissue damage, prior to reapplying the light beam to the retina.

16. The process of claim 14, wherein the generating step comprises the step of generating a light beam having a wavelength of approximately 810 nm.

17. The process of claim 14, wherein generating step includes the step of generating a micropulsed laser light beam having a pulse length of approximately 300 milliseconds or less.

18. The process of any of claims 14-17, wherein the intensity of the laser light beam is 100-590 watts per square centimeter.

19. The process of claim 18, wherein the intensity of the laser light beam is approximately 350 watts per square centimeter.

20. The process of claim 14, wherein true subthreshold phototherapy is achieved.

21. The process of any of claims 14-17, including the step of applying the laser light beam to the retina at 18 to 55 times the American National Standards Institute Maximum Permissible Exposure level.

22. A process for treating a retinal disease or disorder, comprising the steps of:
    generating a micropulsed laser light beam having a duty cycle of less than 10% or less, a wavelength of at least 532 nm, and an intensity and pulse length to create harmless, subthreshold photocoagulation when the light beam is applied to retinal or foveal tissue;
    creating a geometric object or pattern of a plurality of simultaneously generated treatment light spots from the light beam; and
    applying the geometric object or pattern of light spots to at least a portion of the retina, including at least a portion of the fovea, without damaging retinal or foveal tissue.

23. The process of claim 20, wherein the intensity of the laser light beam is between 100-590 watts per square centimeter.

24. The process of claim 20, including the step of applying the laser light beam to the retina at 18 to 55 times the American National Standards Institute Maximum Permissible Exposure level.

25. The process of claim 20, including the step of applying the laser light beam to substantially the entire retina and fovea.

26. The process of claim 20, including the step of controllably moving the geometric object or pattern of light spots to treat adjacent retinal tissue.

27. The process of claim 26, wherein the moving step includes the steps of incrementally moving the light beam geometric object or pattern a sufficient distance from where the light beam was previously applied to the retina, to avoid thermal tissue damage, prior to reapplying the light beam to the retina.

28. The process of any of claims 22-25, wherein the laser light beam has a wavelength between 750 nm-1300 nm.

29. The process of claim 28, wherein the laser light beam has a wavelength of approximately 810 nm.

30. The process of claim 22, wherein the micropulsed laser light beam has a duty cycle of approximately 5% or less.

31. The process of any of claims 22-25, wherein generating step includes the step of generating a micropulsed laser light beam having a pulse length of approximately 500 milliseconds or less.

* * * * *